United States Patent [19]

Yokoyama

[11] Patent Number: 4,524,146

[45] Date of Patent: Jun. 18, 1985

[54] CERTAIN -2-HETEROCYCLE SUBSTITUTED PYRAZOLOQUINOLINES

[75] Inventor: Naokata Yokoyama, Cliffside, N.J.

[73] Assignee: Ciba-Geigy Corporation, Ardsley, N.Y.

[21] Appl. No.: 447,825

[22] Filed: Dec. 8, 1982

[51] Int. Cl.³ .................. A61K 31/505; C07D 401/14
[52] U.S. Cl. .................... 514/273; 514/269; 514/274; 514/293; 544/310; 544/316; 544/317; 544/319; 544/320; 544/321; 544/328; 544/331; 546/82
[58] Field of Search .................. 546/82; 544/310, 316, 544/317, 320, 321, 319, 328, 331; 424/251, 258

[56] References Cited

U.S. PATENT DOCUMENTS 4,312,870  1/1982  Yokoyama .......................... 546/82

FOREIGN PATENT DOCUMENTS 1926023  11/1969  Fed. Rep. of Germany ........ 546/82

OTHER PUBLICATIONS

Lal, et al., "Indian Jour. Chem.", vol. 15B, 1977, pp. 359–363.
Life Sciences 30, 363, 2245, 1982.
J. Med. Chem. 25, 337, 1982.

European Patent Application 22,078 published 1/7/81, Abstract only enclosed.
Scrip No. 731, Sep. 27, 1982, p. 15.

Primary Examiner—Glennon H. Hollrah
Assistant Examiner—James H. Turnipseed
Attorney, Agent, or Firm—Norbert Gruenfeld

[57] ABSTRACT

Pyrazolo[4,3-c]quinolin-3-ones of the formula

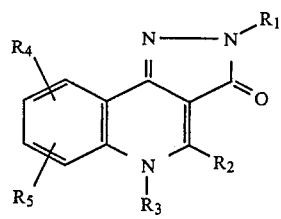

e.g. wherein $R_1$ is an aromatic heterocyclic radical selected from quinolyl, isoquinolyl, pyrimidyl and thiazolyl, or such said heterocyclic radical mono- or di-substituted by lower alkyl, lower alkoxy or halogen; $R_2$ and $R_3$, each independently, represents hydrogen or lower alkyl; $R_4$ and $R_5$, each independently, represents hydrogen, lower alkyl, lower alkoxy, halogen or trifluoromethyl; and pharmaceutically acceptable salts thereof, are benzodiazepine receptor modulators.

18 Claims, No Drawings

CERTAIN -2-HETEROCYCLE SUBSTITUTED PYRAZOLOQUINOLINES

BACKGROUND OF THE INVENTION

The Applicant's U.S. European Patent Application No. 22,078 and substantially equivalent U.S. Pat. No. 4,312,870 are directed to substituted or unsubstituted 2-(phenyl and pyridyl)-pyrazolo[4,3-c]quinolin-3-ones.

SUMMARY OF THE INVENTION

The present invention is directed to 2-substituted pyrazolo[4,3-c]quinolin-3-ones of the formula IA or IB which are benzodiazepine receptor ligands and modulators demonstrating useful nervous system regulatory activity, e.g. psychoactive, such as anxiolytic, and anticonvulsant activity.

The foregoing attributes render compounds of this invention particularly useful when administered, alone or in combination, to mammals for the treatment of e.g. nervous system disorders, such as anxiety, and convulsive conditions (epilepsy). Compounds of the invention may also be useful as antidepressants, as somnolytics, as appetite suppressants, as antagonists (antidotes) of the effects of benzodiazepine drugs on the central nervous system, as well as antagonists of the sedative effects of alcohol and benzodiazepine drugs in combination.

DETAILED DISCLOSURE OF THE INVENTION

This invention relates to novel pyrazolo[4,3-c]quinoline-3-ones, useful as e.g. benzodiazepine receptor modulators, processes for preparing the same, pharmaceutical compositions comprising said compounds and methods of treating e.g. nervous system disorders by administration of said compounds and compositions to mammals.

Particularly the invention relates to compounds of formula IA or IB

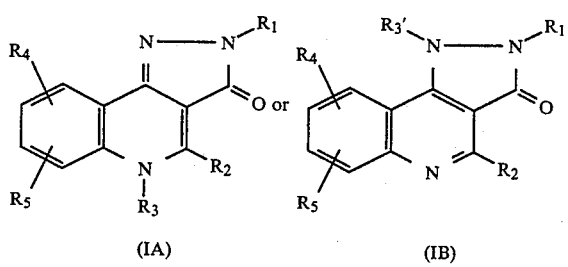

(IA)            (IB)

wherein $R_1$ represents a five-membered unsaturated heterocyclic radical containing one hetero atom selected from sulfur, oxygen and nitrogen, or containing two hetero atoms comprising one nitrogen atom and one member selected from nitrogen, sulfur and oxygen; or $R_1$ represents an unsaturated six membered heterocyclic radical containing two nitrogen atoms; or $R_1$ represents a bicyclic benzo-fused five membered unsaturated heterocyclic radical containing one hetero atom selected from sulfur, oxygen and nitrogen; or $R_1$ represents a bicyclic benzo-fused five membered unsaturated heterocyclic radical containing two hetero atoms comprising one nitrogen atom and one member selected from nitrogen, sulfur and oxygen; or $R_1$ represents a bicyclic benzo-fused six membered unsaturated heterocyclic radical containing one or two nitrogen atoms; or $R_1$ represents any of said heterocyclic radicals mono- or di-substituted by lower alkoxy, lower alkyl or halogen; $R_2$, $R_3$ and $R_3'$, each independently, represents hydrogen or lower alkyl; $R_4$ and $R_5$, each independently, represents hydrogen, lower alkyl, lower alkoxy, halogen or trifluoromethyl; or salts thereof.

Preferred are the compounds of formula IA or IB wherein $R_1$ is an aromatic heterocyclic radical selected from quinolyl, isoquinolyl, pyrimidyl, and thiazolyl, or such said heterocyclic radical mono- or di-substituted by lower alkyl, lower alkoxy or halogen; and $R_2$, $R_3$, $R_3'$, $R_4$ and $R_5$ are as defined above; or pharmaceutically acceptable salts thereof.

Further preferred are the compounds of formula IA or IB wherein $R_1$ is an aromatic heterocyclic radical selected from quinolyl, pryimidyl, isoquinolyl and thiazolyl, or such said heterocyclic radical mono-substituted by halogen, lower alkyl or lower alkoxy; $R_2$, $R_3$ and $R_3'$, each independently, is hydrogen or lower alkyl; and $R_4$ and $R_5$, each independently, represents hydrogen or halogen; or pharmaceutically acceptable salts thereof.

One particular embodiment of the invention represents said compounds of formula IA or IB wherein $R_1$ is an aromatic heterocyclic radical selected from quinolyl, isoquinolyl, pyrimidyl and thiazolyl, or said radical monosubstituted by methyl, methoxy, fluoro or chloro; $R_2$, $R_3$, $R_3'$ and $R_5$ are hydrogen; and $R_4$ is hydrogen, fluoro or chloro; or pharmaceutically acceptable salts thereof.

One preferred embodiment of the invention is presented by compounds of formula IA or IB wherein $R_1$ is 2-, 3- or 4-quinolyl unsubstituted or mono-substituted by lower alkoxy or halogen; $R_2$, $R_3$ and $R_3'$, each independently, is hydrogen or lower alkyl; and $R_4$ and $R_5$, each independently, represents hydrogen or halogen; or pharmaceutically acceptable salts thereof.

Further preferred are said compounds, wherein $R_1$ is 2-quinolyl, 3-quinolyl or 7-chloro-4-quinolyl; $R_2$, $R_3$, $R_3'$ and $R_5$ are hydrogen; and $R_4$ is hydrogen, 8-fluoro or 8-chloro; or pharmaceutically acceptable salts thereof.

Another preferred embodiment of the invention is represented by compounds of formula IA or IB wherein $R_1$ is 2-, 4-, 5- or 6-pyrimidyl unsubstituted or mono-substituted by lower alkyl, lower alkoxy or halogen; $R_2$, $R_3$ and $R_3'$, each independently, is hydrogen or lower alkyl; and $R_4$ and $R_5$, each independently, represents hydrogen or halogen; or pharmaceutically acceptable salts thereof. Preferred are said compounds wherein $R_1$ represents 2-pyrimidyl, 5-(lower alkyl, lower alkoxy, halo)-2-pyrimidyl, 4-pyrimidyl, 5-pyrimidyl or 2-(lower alkyl, lower alkoxy)-5-pyrimidyl.

Further preferred are said compounds wherein $R_1$ is 2-pyrimidyl, 5-(methyl, methoxy or chloro)-2-pyrimidyl, 4-pyrimidyl or 5-pyrimidyl; $R_2$, $R_3$, $R_3'$ and $R_5$ are hydrogen; and $R_4$ is hydrogen, 8-fluoro or 8-chloro; or pharmaceutically acceptable salts thereof.

A further preferred embodiment of the invention is represented by compounds of formula IA or IB wherein $R_1$ is 2-thiazolyl or 2-thiazolyl mono-substituted by lower alkyl, lower alkoxy or halogen; $R_2$, $R_3$ and $R_3'$, each independently is hydrogen or lower alkyl; and $R_4$ and $R_5$, each independently, represents hydrogen or halogen; or pharmaceutically acceptable salts thereof.

Further preferred are said compounds wherein $R_1$ is 2-thiazolyl or 5-(methyl, methoxy or chloro)-2-thiazolyl; $R_2$, $R_3$, $R_3'$ and $R_5$ are hydrogen; and $R_4$ is hydrogen, 8-fluoro or 8-chloro; or pharmaceutically acceptable salts thereof.

Another preferred embodiment of the invention is represented by compounds of formula IA or IB wherein $R_1$ is 1-, 3- or 4-isoquinolyl unsubstituted or mono-substituted by lower alkyl, lower alkoxy or halogen; $R_2$, $R_3$ and $R_3'$, each independently is hydrogen or lower alkyl; and $R_4$ and $R_5$, each independently, represents hydrogen or halogen; or pharmaceutically acceptable salts thereof.

Further preferred are said compounds wherein $R_1$ is 1-isoquinolyl; $R_2$, $R_3$, $R_3'$ and $R_5$ are hydrogen; and $R_4$ is hydrogen, 8-fluoro or 8-chloro; or pharmaceutically acceptable salts thereof.

The general definitions used herein have the following meaning within the scope of the present invention.

The term "lower" referred to above and hereinafter in connection with organic radicals or compounds respectively defines such with up to and including 7, preferably up and including 4 and advantageously one or two carbon atoms.

Halogen is preferably fluoro or chloro, but may also be bromo or iodo.

A lower alkyl group or such present in said lower alkoxy, or other alkylated groups, is above all methyl, but also ethyl, n- or i-(propyl, butyl, pentyl, hexyl or heptyl), e.g. 2-methylpropyl or 3-methylbutyl.

The compounds of the invention wherein $R_3$ and $R_3'$ are hydrogen may be represented by either of the tautomeric structure IA or IB, preferably structure IA; furthermore said 3-oxo compounds may, under certain conditions, also exist as the 3-hydroxy tautomers; all of these tautomers are within the scope of the present invention. Said compounds form, especially in the form of the 3-hydroxy compounds, salts with strong bases, and the salts are preferably alkali metal, e.g. sodium or potassium salts of the 1- or 5-unsubstituted compounds ($R_3$ and $R_3'$=H).

Furthermore the compounds of Formula IA or IB, form acid addition salts, which are preferably such of pharmaceutically acceptable inorganic or organic acids, such as strong mineral acids, for example hydrohalic, e.g. hydrochloric or hydrobromic acid; sulfuric, phosphoric or nitric acid; aliphatic or aromatic carboxylic or sulfonic acids, e.g. acetic, propionic, succinic, glycolic, lactic, malic, tartaric, gluconic, citric, maleic, fumaric, hydroxymaleic, pyruvic, phenylacetic, benzoic, 4-aminobenzoic, anthranilic, 4-hydroxybenzoic, salicylic, 4-aminosalicylic, pamoic, nicotinic; methanesulfonic, ethanesulfonic, hydroxyethanesulfonic, benzenesulfonic, p-toluenesulfonic, naphthalenesulfonic, sulfanilic, cyclohexylsulfamic acid; or ascorbic acid.

The compounds of the invention exhibit valuable pharmacological properties, e.g. nervous system regulator effects, by inter alia modulating the benzodiazepine receptor activity in mammals. The compounds are thus useful for the treatment of nervous system diseases, e.g. those responsive to benzodiazepine receptor modulation.

The compounds of the invention bind to the benzodiazepine receptor and exhibit e.g. anxiolytic and/or anticonvulsant effects, or antagonism of the effects of benzodiazepine drugs. Said effects are demonstrable by in vitro and vivo tests, using advantageously mammals, e.g. mice, rats, or monkeys, as test objects. Said compounds can be applied to them enterally or parenterally, advantageously orally, or subcutaneously, intravenously or intraperitoneally, for example, within gelatin capsules or in the form of starchy suspensions or aqueous solutions or suspensions respectively. The applied dosage may range between 0.1 and 100 mg/kg/day, preferably between about 0.1 and 50 mg/kg/day, advantageously between about 1 and 30 mg/kg/day.

The benzodiazepine receptor binding properties indicative of the nervous system regulatory activity of said new compounds are determined in the receptor binding assay in vitro, e.g. as described in Nature 266, 732 (1977) or Proc. Nat. Acad. Sci. USA 74, 3805 (1977). Diazepam binds specifically and with high affinity to crude synaptosomal membrane preparations from rat fore-brain. This binding is inhibited by other anxiolytic compounds. When tritiated diazepem is used, the interaction of other drugs with said receptor can be readily assessed thus: membranes from rat fore-brain are incubated at 0°–5° for 30 minutes with 2 nM tritiated diazepam and various concentrations of the test substance in a buffer medium maintained at pH7.5. Solutions of the various concentrations of test substances are prepared by dilution of a 4.2 mM stock solution in dimethylacetamide-ethanol (1:10) with 50 mM pH7.5 Tris-HCl buffer. The membranes, containing the receptors with various amounts of tritiated diazepam, are filtered onto glass fiber filters, which are then analyzed in a liquid scintillation counter. The concentration of the compounds of this invention, required to inhibit the specific binding of 2 nM of tritiated diazepam by 50%, i.e. the $IC_{50}$, is determined graphically.

In vivo benzodiazepine receptor binding is determined essentially as described in Eur. J. Pharmacol. 48, 213 (1978) and Nature 275, 551 (1978).

Test compounds in a corn starch vehicle are administered orally or intraperitoneally to mice or rats. Thirty minutes later, 3H-flunitrazepam (2 nmoles/Kg in saline) is injected into the tail vein, and the animals are sacrificed 20 minutes after injection of the flunitrazepam. The brains are then assayed by determining radioactivity in a liquid scintillation counter for binding of the radioligand to the receptors. A decrease in the binding of 3H-flimotrazepam in the drug-treated animals (as compared with the binding observed in animals treated with vehicle alone) is indicative of benzodiazepine receptor binding by the test compound.

Anxiolytic effects are observed, for example, according to the Cook-Davidson conflict procedure, using male Wistar rats which are maintained at 80% of normal body weight by dietary-, but not water-restriction. They are trained to press a lever within a conditioning chamber, also containing a liquid dipper, a house light, a speaker and a grid-floor. Both lever and grid are connected to an electrical shock source and the chamber is situated in a sound-attenuated room in which a white noise-source is activated during testing, in order to mask any extraneous auditory cues. Each session of 47 minutes duration consists of two alternating schedules. The first is a Variable Interval (VI) schedule of 30 seconds, lasting for 5 minutes, during which a sweetened, condensed milk reinforcement is delivered following the first lever-press after an average of 30 seconds have elapsed, and a drug-induced decrement of this performance is taken as an indication of a neurological deficit. Immediately following the VI-schedule both a 1000 Hz tone and a light-cue are activated, indicating the commencement of the second Fixed Ratio (FR) schedule, lasting for 2 minutes, wherein the milk reinforcement is delivered concomitant with an electric foot shock immediately following the tenth response, thereby establishing a conflict situation. The intensity of said shock ranges between 2.0 and 3.6 mA, varying with each animal, in order to adjust them to about 25-100 responses during this schedule over the entire session. A drug-induced enhancement of performance during the FR-schedule is taken as indication of antianxiety effects. This increased performance is measured by the increased number of electric foot shocks taken during six FR sessions lasting 2 minutes each.

Anticonvulsant effects are observed, for example in the standard Metrazole (pentylenetetrazole) and maximal electroshock tests for assessing anticonvulsant activity, e.g. orally in the rat.

Male Wistar rats (130-175 g) are fasted for 18 hours but allowed water ad libitum prior to testing. The test compound is administered in a cornstarch vehicle by oral intubation in a volume of 10 ml/Kg of body weight. One hour after administration of the test compounds, the animals are administered intravenously (caudal vein) a dose of 24 mg/Kg of Metrazole in water in a volume of 2.5 mg/Kg of body weight. The rats are immediately placed in plexiglas cylinders and observed for clonic seizures of at least 5 seconds duration during the next 60 seconds. The $ED_{50}$ is the dose at which half the animals are protected from Metrazole induced clonic seizures during the observation periods.

Benzodiazepine antagonism is measured by the antagonism of the anticonvulsant activity of diazepam in the rat Metrazole model. Diazepam (5.4 mg/kg/po) and test compound are administered 1 hour before the Metrazole challenge.

In the maximal electroshock procedure for assessing anticonvulsant activity in rats, seizures are induced by applying 150 mA of electric current for 0.2 sec. through corneal electrodes two hours after oral administration of test compound as described for the Metrazole test above. The $ED_{50}$ is the dose at which half the animals are protected from electroshock induced seizures during the 5 seconds observation period.

Illustrative of the invention the compounds of examples 1, 2 and 4 exhibit an $IC_{50}$ of about 6 nM, 2 nM and 0.3 nM respectively in the in vitro benzodiazepine receptor assay. Furthermore, e.g. the compound of example 4 inhibits flunitrazepam binding in vivo at a dose of about 30 mg/kg i.p.

The compounds of the invention also act as adenosine antagonists. Such activity is assessed by determination of inhibition of adenosine activation of adenylate cyclase in vesicular preparations from guinea pig brains, essentially as described in J. Neurochem. 22, 1031 (1974).

Accordingly, the compounds of the invention are useful nervous system active agents, e.g. as benzodiazepine receptor modulators for example in the treatment or management of nervous systems disorders such as anxiety, convulsive conditions (epilepsy) and depression in mammals. They are also useful intermediates in the preparation of other valuable products, especially of pharmacologically active pharmaceutical compositions.

The compounds of the invention, the compounds of formula IA or IB and salts, derivatives or tautomers thereof, are advantageously prepared by methods known per se, according to the following processes:

(a) reacting a compound of formula II (II)

wherein $R_2$, $R_3$, $R_4$ and $R_5$ have meaning as defined hereinabove and Y is lower alkoxy with a compound of the formula $$R_3'\text{-NH-NH-}R_1 \qquad (III)$$

wherein $R_1$ has meaning as defined hereinabove and $R_3'$ is hydrogen;

(b) reacting a compound of the formula IV (IV)

wherein $R_2$, $R_4$ and $R_5$ have meaning as defined in said claim 1; X represents reactive etherified or esterified hydroxy; and Y represents lower alkoxy;
 with a compound of formula III wherein $R_1$ has meaning as defined hereinabove and $R_3'$ represents hydrogen or lower alkyl;

(c) ring closing a compound of formula IV wherein X is $-NR_3'-NHR_1$ and Y is lower alkoxy or hydroxy; or X is hydroxy, reactive esterfied or etherified hydroxy, and Y is $-NR_1NHR_3'$; and wherein $R_1$, $R_2$, $R_3'$, $R_4$ and $R_5$ have meaning as defined in formula I; and if desired, converting a resulting compound of formula IA or IB into another compound of the invention; and, if desired, converting a resulting compound of formuls IA or IB into a salt thereof or liberating a free compound from such salt.

The compounds of the invention may also be prepared analogous to other methods known per se, e.g. those disclosed in U.S. Pat. No. 4,312,870.

The condensation according to process (a) is carried out preferably at a temperature range of about 50° to 180°, advantageously in the presence of inert solvents such as aliphatic or aromatic hydrocarbons and ethers such as toluene, xylene, biphenyl and/or diphenyl ether, advantageously e.g. while distilling off the alkanol and water generated, or in the presence of dehydrating agents, such as molecular sieves.

The starting materials of formula II are known or may be prepared by methods well-known to the art, e.g. according to J. Am. Chem. Soc. 69, 371 (1947).

The starting materials of formula III are also known or are prepared by methods well known to the art.

The condensation according to proces (b) above is carried out with an excess or equivalent amount of a compound of formula III advantageously and depending on the nature of the reactants at temperatures between about 50° and 200° and preferably in an inert solvent e.g. a lower alkanol such as amyl alcohol, n-butyl alcohol or ethanol, an aliphatic or aromatic hydrocarbon such as toluene, xylene or biphenyl, an aromatic ether, such as diphenyl ether or mixtures thereof.

The starting materials of formula IV are known or are prepared by methods well known to the art, e.g. according to U.S. Pat. No. 4,312,870 or J. Chem. Soc. 1951, 1389.

In said starting materials of formula IV, X represents reactive esterified hydroxy being preferably halogen such as chloro or bromo, lower alkylsulfonyloxy such as methanesulfonyloxy, or reactive etherified hydroxy being preferably lower alkoxy such as methoxy, or aryloxy such as phenoxy.

The ring closure of compounds of formula IV, according to process (c) is carried out preferably at a temperature range of about 50° to 200°, advantageously in the presence of inert solvents such as aliphatic or aromatic hydrocarbons, such as toluene, xylene or biphenyl, ethers such as diphenyl ether, alkanols such as n-butanol, with or without a base (such as an alkali metal alkoxide, e.g. sodium ethoxide), a dehydrating agent (such as molecular sieves) or a condensing agent (such as N-ethoxycarbonyl-2-ethoxy-1,2-dihydroquinoline), depending on the nature of X and Y.

Advantageously a condensing agent or dehydrating agent is used for the ring closure of compounds of formula IV wherein Y represents hydroxy.

The starting materials for process (c) of formula IV wherein X is $-NR_3'-NHR_1$ and Y is lower alkoxy or hydroxy may be obtained by condensation of a compound of formula IV wherein X represents reactive etherified or esterified hydroxy and Y represents lower alkoxy with a hydrazine of formula III wherein $R_1$ and $R_3'$ are as previously described in an inert solvent, preferably at a temperature range of about 0° to 75°, and hydrolysis if so required.

The hydrazide starting materials of formula IV wherein X is hydroxy, esterified or etherified hydroxy and Y is $-NR_1NHR_3'$ are advantageously prepared by condensing a compound of formula IVa

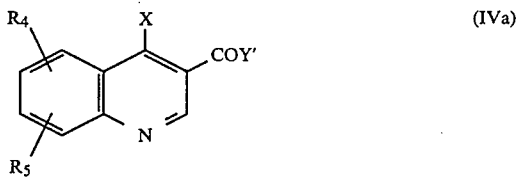

(IVa)

wherein X represents hydroxy, esterified or etherified hydroxy, COY' represents a reactive functionalized carboxy group (such as an acid halide or a mixed anhydride group) and $R_4$ and $R_5$ are as previously described, with a hydrazine of formula III or with an $NHR_3'$-acylated derivative thereof (such as $HNR_1-NR_3'-COCF_3$) and subsequently deacylating the resulting acyl substituted hydrazide.

A preferred starting material of formula IVa is the appropriately substituted 4-chloroquinoline-3-carboxylic acid chloride.

The compounds of the invention so obtained can be converted into other compounds of formuls IA or IB according to known methods.

For example compounds of formula IA or IB with $R_3$ or $R_3' = H$ can be 1-substituted with reactive esters of $R_3$-OH, e.g. such of hydrohalic, aliphatic or aromatic sulfonic acids, such as $R_3$-(halides, sulfates, aliphatic or aromatic sulfonates), e.g. methyl iodide, dimethyl sulfate, methyl mesylate or tosylate, in order to yield the 1-substituted compounds of Formula IB. Those of Formula IA are similarly obtained from the corresponding alkali metal salts, e.g. the sodium salt, whereby 5-substitution occurs. The metal derivative intermediates are obtained by metallation with reactive organometallic agents such as lithium diisopropylamide, with alkali metal alkoxides such as sodium methoxide, or thallous ethoxide, or alkali metal hydrides such as sodium or potassium hydride.

Finally, the compounds of the invention are either obtained in the free form, or as a salt thereof whenever applicable. Any resulting free base can be converted into a corresponding acid addition salt, preferably with the use of a pharmaceutically acceptable acid or anion exchange preparation, or any resulting salt can be converted into the corresponding free base, for example, with the use of a stronger base, such as a metal or ammonium hydroxide or a basic salt, e.g. an alkali metal hydroxide or carbonate, or a cation exchange preparation. Said acid addition salts are preferably such of pharmaceutically acceptable inorganic or organic acids described previously.

Compounds of formula IA or IB with $R_3$ or $R_3'$ being hydrogen can also be converted into the corresponding metal salts by e.g. treatment with the alkaline or alkaline earth metal hydroxides or carbonates.

These or other salts, for example, the picrates, can also be used for purification of the bases obtained; the bases are converted into salts, the salts are separated and the bases are liberated from the salts.

In view of the close relationship between the free compounds and the compounds in the form of their salts, whenever a compound is referred to in this context, a corresponding salt is also intended, provided such is possible or appropriate under the circumstances.

The compounds including their salts, can also be obtained in the form of their hydrates or include other solvents used for crystallization.

In case mixtures of isomers of any the above compounds, e.g. of formula I to IV are obtained, these can be separated into the single isomers by methods in themselves known, e.g. by fractional distillation, crystallization and/or chromatography.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, preferably near the boiling point of the solvents used, at atmospheric or superatmospheric pressure.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or pure isomers. Mainly those starting materials should be used in said reactions, that lead to the formation of those compounds, indicated above as being especially valuable.

The pharmacologically active compounds of the invention are useful in the manufacture of the pharmaceutical compositions comprising an effective amount thereof in conjunction or admixture with excipients suitable for either enteral or parenteral application. Preferred are tablets and gelatin capsules comprising the active ingredient together with (a) diluents, e.g.

lactose, dextrose, sucrose, mannitol, sorbitol, cellulose and/or glycine; (b) lubricants, e.g. silica, talcum, stearic acid, its magnesium or calcium salt and/or polyethyleneglycol; for tablets, also (c) binders, e.g., magnesium aluminum silicate, starch paste, gelatin, tragacanth, methylcellulose, sodium carboxymethylcellulose and/or polyvinylpyrrolidone; if desired, (d) disintegrants, e.g. starches, agar, alginic acid or its sodium salt, or effervescent mixtures; and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient. A unit dosage for a mammal of about 50 to 70 Kg weight may contain between about 4 and 100 mg of the active ingredient.

The following examples are intended to illustrate the invention and are not to be construed as being limitations thereon. Temperatures herein are given in degrees Centigrade, and all parts whenever given are parts by weight. If not mentioned otherwise, all evaporations are performed under reduced pressure, preferably between about 15 and 100 mm Hg. Proportions whenever given for liquids are in parts by volume.

EXAMPLE 1

A solution of 2.36 g of ethyl 4-chloroquinoline-3-carboxylate and 1.46 g of 2-hydrazinopyrimidine in 80 ml of ethanol is refluxed for 2 hours and 30 minutes. The resulting slurry is cooled down to 5°, then filtered and the resulting product is taken up in 20 ml of N sodium hydroxide and sufficient water to effect solution. Ammonium chloride (10 g) is added, the resulting precipitate is collected, and is washed three times with ethanol and three times with ether to yield 2-(2-pyrimidyl)-pyrazolo[4,3-c]quinolin-3(5H)-one, m.p. above 360°; IR (KBr) 800, 817, 844, 886 cm$^{-1}$.

EXAMPLE 2

A solution of 2.0 of ethyl 4-chloro-6-fluoroquinolin-3-carboxylate and 0.95 g of 2-hydrazinopyrimidine in 40 ml of 95% ethanol is heated under reflux for 16 hours. The reaction mixture is filtered and the resulting solid is taken up in 20 ml of N sodium hydroxide and sufficient water to effect solution. Ammonium chloride (10.7 g) is added, the resulting precipitate is collected, washed with water and dried to yield 8-fluoro-2-(2-pyrimidyl)-pyrazolo[4,3-c]quinolin-3(5H)-one, as a hydrate, m.p. above 350°; IR (KBr) 800, 829, 870, 880 cm$^{-1}$.

The starting material, ethyl 4-chloro-6-fluoroquinolin-3-carboxylate, is prepared according to U.S. Pat. No. 4,312,870.

EXAMPLE 3

A solution of 11.8 g of ethyl 4-chloroquinoline-3-carboxylate and 8.7 g of 3-hydrazinoquinoline is refluxed for 5½ hours in 300 ml of xylene. The reaction mixture is allowed to stand for 16 hours at 23°. The solvent is decanted from an oily solid. This solid is slurried twice in 80 ml of xylene, the solvent is decanted and the residue is stirred for 1 hour in 150 ml of 1N sodium hydroxide, 150 ml of water and 220 ml of xylene. The mixture is filtered, the aqueous layer is separated and 12 g of ammonium chloride is added while stirring. The resulting slurry is heated on the steam bath for one hour, allowed to cool down to 30° and then filtered. The solid is washed three times with water, twice with ether-acetone (2:1) and twice with ether. Recrystallization from dimethylformamide gives 2-(3-quinolyl)pyrazolo[4,3-c]quinolin-3(5H)-one, m.p. above 350°; IR (KBr) 802, 852, 858, 882, 895 cm$^{-1}$.

EXAMPLE 4

A mixture of ethyl 4-(2-thiazolylhydrazino)-quinoline-3-carboxylate hydrochloride (1.16 g) and 20 ml of n-butanol is heated under reflux for 5 hours, cooled to room temperature and filtered. The resulting solid is washed with ethanol and ether, and dried to yield 2-(2-thiazolyl)-pyrazolo[4,3-c]quinolin-3(5H)-one, m.p. over 350°; IR (KBr) 818, 840, 871, 891 cm$^{-1}$.

The starting material is prepared as follows:

A solution of 1.63 g of ethyl 4-chloroquinoline-3-carboxylate and 0.80 g of 2-hydrazinothiazole in 22 ml of methanol is stirred for 26 hours at 23°; 22 ml of diethyl ether is added to the resulting slurry, which is then filtered. The precipitate is washed once with methanol-ether (1:1) and once with ether to yield ethyl 4-(2-thiazolylhydrazino)-quinoline-3-carboxylate hydrochloride as a yellow solid which is used directly in the above cyclization.

EXAMPLE 5

Compounds which are prepared analogous to the methods illustrated by the previous examples:

EXAMPLE

5/a 8-Fluoro-2-(7-chloro-4-quinolyl)-pyrazolo[4,3-c]quinolin-3(5H)-one, m.p. above 350°; IR (KBr) 822, 852, 874, 899 cm$^{-1}$.

EXAMPLE

5/b 8-Fluoro-2-(2-thiazolyl)-pyrazolo[4,3-c]quinolin-3(5H)-one, m.p. above 350° C.; IR (KBr) 820, 832, 848, 856, 876 cm$^{-1}$.

5/c 2-(2-Quinolyl)-pyrazolo[4,3-c]quinolin-3(5H)-one, m.p. above 350°; IR (KBr) 801, 833, 882 cm$^{-1}$.

5/d 2-(7-chloro-4-quinolyl)-pyrazolo[4,3-c]quinolin-3(5H)-one, m.p. above 350°; IR (KBr) 822, 857, 870, 897 cm$^{-1}$.

EXAMPLE 6

Compounds of formula IA wherein $R_2$, $R_3$, $R_5$ are hydrogen which can be prepared analogous to the methods illustrated by the previous examples.

| Example | $R_1$ | $R_4$ |
|---|---|---|
| 6/a | 4-pyrimidyl | H |
| 6/b | 5-pyrimidyl | H |
| 6/c | 6-pyrimidyl | H |
| 6/d | 2-pyrimidyl | 8-Cl |
| 6/e | 5-methoxy-2-pyrimidyl | H |
| 6/f | 5-chloro-2-pyrimidyl | H |
| 6/g | 5-methyl-2-pyrimidyl | H |
| 6/h | 1-isoquinolyl | H |
| 6/i | 1-isoquinolyl | 8-F |

EXAMPLE 7

Preparation of 10,000 tablets each containing 10 mg of the active ingredient:

| | |
|---|---|
| 2-(2-Pyrmidyl)-pyrazolo[4,3-c]quinolin-3(5H)—one | 100.00 g |
| Lactose | 1,157.00 g |
| Corn Starch | 75.00 g |
| Polyethylene glycol 6,000 | 75.00 g |
| Talcum powder | 75.00 g |
| Magnesium stearate | 18.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

EXAMPLE 8

Preparation of 10,000 capsules each containing 25 mg of the active ingredient:

| Formula: | |
|---|---|
| 2-(2-thiazolyl)-pyrazolo[4,3-c]quinolin-3(5H)—one | 250.0 g |
| Lactose | 1,650.0 g |
| Talcum powder | 100.0 g |

Procedure

All the powders are passed through a screen with openings of 0.6 mm. Then the drug substance is placed in a suitable mixer and mixed first with the talcum, then with the lactose until homogenous. No. 3 capsules are filled with 200 mg each, using a capsule filling machine.

Analogously tablets or capsules are prepared from the remaining compounds of the invention, e.g. those illustrated by the examples herein.

What is claimed is:

1. A compound of the formula

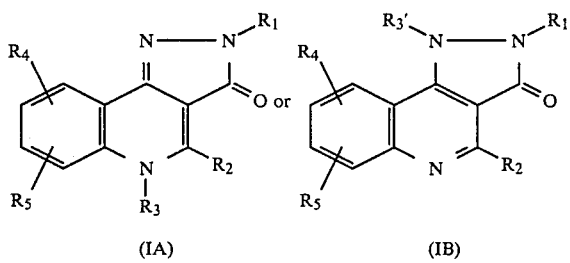

(IA)    (IB)

wherein $R_1$ represents a five-membered unsaturated heterocyclic radical having two hetero atoms comprising one nitrogen atom and one member selected from nitrogen, sulfur and oxygen; or $R_1$ represents an unsaturated six membered heterocyclic radical having two nitrogen atoms; or $R_1$ represents a bicyclic benzo-fused six membered unsaturated heterocyclic radical having one or two nitrogen atoms; or $R_1$ represents any of said heterocyclic radicals mono- or di-substituted by lower alkoxy, lower alkyl or halogen; $R_2$, $R_3$ and $R_3'$, each independently, represents hydrogen or lower alkyl; $R_4$ and $R_5$, each independently, represents hydrogen, lower alkyl, lower alkoxy, halogen or trifluoromethyl; or a pharmaceutically acceptable salt thereof.

2. A compound according to claim 1 of formula IA or IB wherein $R_1$ is an aromatic heterocyclic radical selected from quinolyl, isoquinolyl, pyrimidyl and thiazolyl, or such said heterocyclic radical mono- or di-substituted by lower alkyl, lower alkoxy or halogen; and $R_2$, $R_3$, $R_3'$, $R_4$ and $R_5$ have the meanings given in claim 1; or a pharmaceutically acceptable salt thereof.

3. A compound according to claim 2 of formula IA or IB wherein $R_1$ is an aromatic heterocyclic radical selected from quinolyl, pyrimidyl, isoquinolyl and thiazolyl, or such said heterocyclic radical mono-substituted by halogen, lower alkyl or lower alkoxy; $R_2$, $R_3$ and $R_3'$, each independently, is hydrogen or lower alkyl; and $R_4$ and $R_5$, each independently, represents hydrogen or halogen; or a pharmaceutically acceptable salt thereof.

4. A compound according to claim 3 of formula IA or IB wherein $R_1$ is 2-, 3- or 4-quinolyl unsubstituted or mono-substituted by lower alkyl, lower alkoxy or halogen; $R_2$ to $R_5$ are as defined in claim 3; or a pharmaceutically acceptable salt thereof.

5. A compound according to claim 3 of formula IA or IB wherein $R_1$ is 2-, 4-, 5- or 6-pyrimidyl unsubstituted or mono-substituted by lower alkyl, lower alkoxy or halogen; $R_2$ to $R_5$ are as defined in claim 3; or a pharmaceutically acceptable salt thereof.

6. A compound according to claim 3 of formula IA or IB wherein $R_1$ is 2-thiazolyl or 2-thiazolyl mono-substituted by lower alkyl, lower alkoxy or halogen; $R_2$ to $R_5$ are as defined in claim 3; or a pharmaceutically acceptable salt thereof.

7. A compound according to claim 3 of formula IA or IB wherein $R_1$ is 1-, 3- or 4-isoquinolyl unsubstituted or mono substituted by lower alkyl, lower alkoxy or halogen; $R_2$ to $R_5$ are as defined in claim 3; or a pharmaceutically acceptable salt thereof.

8. A compound according to claim 3 of formula IA or IB wherein $R_1$ is an aromatic heterocyclic radical selected from quinolyl, isoquinolyl, pyrimidyl and thiazolyl, or said radical monosubstituted by methyl, methoxy, fluoro or chloro; $R_2$, $R_3$, $R_3'$ and $R_5$ are hydrogen; and $R_4$ is hydrogen, fluoro or chloro; or a pharmaceutically acceptable salt thereof.

9. A compound of claim 4 wherein $R_1$ is 2-quinolyl, 3-quinolyl or 7-chloro-4-quinolyl; $R_2$, $R_3$, $R_3'$ and $R_5$ are hydrogen; and $R_4$ is hydrogen, 8-fluoro or 8-chloro; or a pharmaceutically acceptable salt thereof.

10. A compound of claim 5 wherein $R_1$ is 2-pyrimidyl, 5-(methyl, methoxy or chloro)-2-pyrimidyl, 4-pyrimidyl or 5-pyrimidyl; $R_2$, $R_3$, $R_3'$ and $R_5$ are hydrogen; and $R_4$ is hydrogen, 8-fluoro or 8-chloro; or a pharmaceutically acceptable salt thereof.

11. A compound of claim 6 wherein $R_1$ is 2-thiazolyl or 5-(methyl, methoxy or chloro)-2-thiazolyl; $R_2$, $R_3$, $R_3'$ and $R_5$ are hydrogen; and $R_4$ is hydrogen, 8-fluoro or 8-chloro; or a pharmaceutically acceptable salt thereof.

12. A compound of claim 7 wherein $R_1$ is 1-isoquinolyl; $R_2$, $R_3$, $R_3'$ and $R_5$ are hydrogen; and $R_4$ is hydrogen, 8-fluoro or 8-chloro; or a pharmaceutically acceptable salt thereof.

13. A compound of claim 3 being 2-(2-thiazolyl)-pyrazolo[4,3-c]quinolin-3(5H)-one or a pharmaceutical acceptable salt thereof.

14. A compound of claim 3 being 8-fluoro-2-(2-pyrimidyl)pyrazolo-[4,3-c]quinolin-3(5H)one or a pharmaceutically acceptable salt thereof.

15. A compound of claim 3 being 2-(3-quinolyl)-pyrazolo-[4,3-c]quinolin-3-(5H)one or a pharmaceutically acceptable salt thereof.

16. A pharmaceutical composition suitable for oral or parenteral administration to mammals for the treatment of nervous system conditions responsive to the action of a benzodiazepine receptor modulator, comprising an effective amount of a compound of claim 1 in combination with one or more pharmaceutically acceptable carriers.

17. An anxiolytic pharmaceutical composition suitable for oral or parenteral administration to mammals comprising an effective amount of a compound of claim 1 having anxiolytic activity in combination with one or more pharmaceutically acceptable carriers.

18. A method for treating anxiety in mammals which comprises administering to a mammal in need thereof an effective amount of a composition of claim 17.

* * * * *